United States Patent [19]

Rugland et al.

[11] Patent Number: 5,562,723
[45] Date of Patent: Oct. 8, 1996

[54] MEDICAL ELECTRICAL LEAD HAVING A REINFORCED TINE ASSEMBLY

[75] Inventors: Roger E. Rugland, Anoka; Gary H. Hanse, Ham Lake; Annette Hebzynski, Minneapolis, all of Minn.

[73] Assignee: Medtronic, Inc., Minneapolis, Minn.

[21] Appl. No.: 319,190

[22] Filed: Oct. 6, 1994

[51] Int. Cl.⁶ .................................................. A61N 1/05
[52] U.S. Cl. ........................................ 607/126; 607/120
[58] Field of Search .................................... 607/120, 122, 607/123, 125–128; 128/642

[56] References Cited

U.S. PATENT DOCUMENTS

| | | |
|---|---|---|
| 4,506,680 | 3/1985 | Stokes . |
| 4,577,642 | 3/1986 | Stokes . |
| 4,606,118 | 8/1986 | Cannon et al. . |
| 4,711,251 | 12/1987 | Stokes . |
| 4,731,074 | 3/1988 | Rousseau et al. ........................ 623/2 |
| 4,913,164 | 4/1990 | Greene et al. .......................... 607/126 |
| 4,957,118 | 9/1990 | Erlebacher ............................. 607/128 |
| 5,179,962 | 1/1993 | Dutcher et al. ........................ 607/128 |
| 5,238,007 | 8/1993 | Giele et al. ............................ 607/126 |
| 5,282,844 | 2/1994 | Stokes et al. .......................... 607/120 |

*Primary Examiner*—William E. Kamm
*Assistant Examiner*—Jeffrey R. Jastrzab
*Attorney, Agent, or Firm*—Michael J. Jaro; Harold R. Patton

[57] ABSTRACT

A medical lead which has a reinforced tine assembly. In particular, the medical electrical lead of the present invention features an elongated lead body covered by an insulative sheath. Positioned upon the proximal end of the lead body is a terminal assembly. Terminal assembly permits the lead to be connected to a pulse generator. Positioned at the distal end of the lead body is an electrode. Also positioned proximate the electrode is a tine assembly. The tine assembly is preferably made from a insulative bio-compatible material, preferably silicone. The tine assembly further features a reinforcement to prevent the tine assembly from elongating. In the preferred embodiment, a polyester is used to provide reinforcement member.

11 Claims, 1 Drawing Sheet

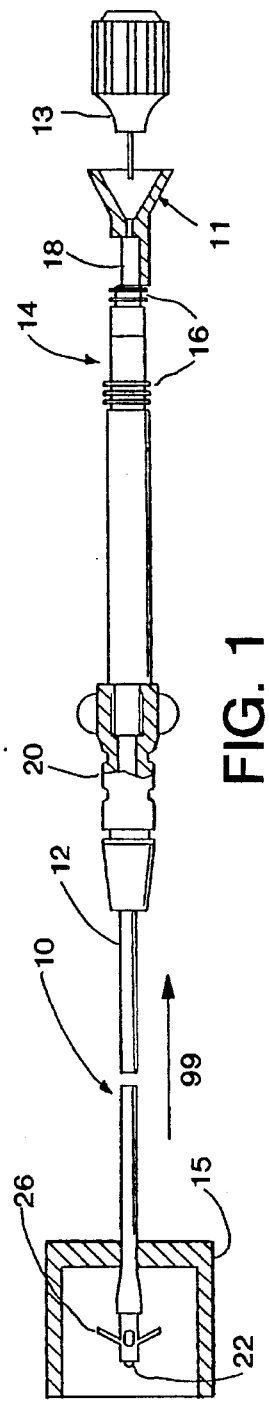
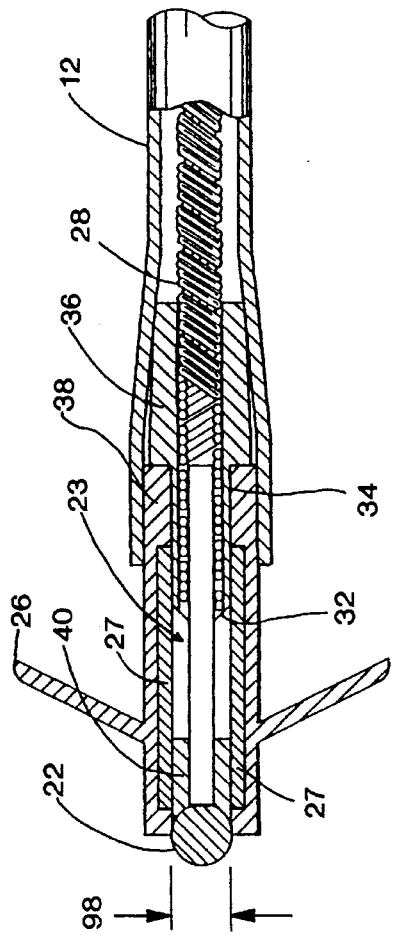
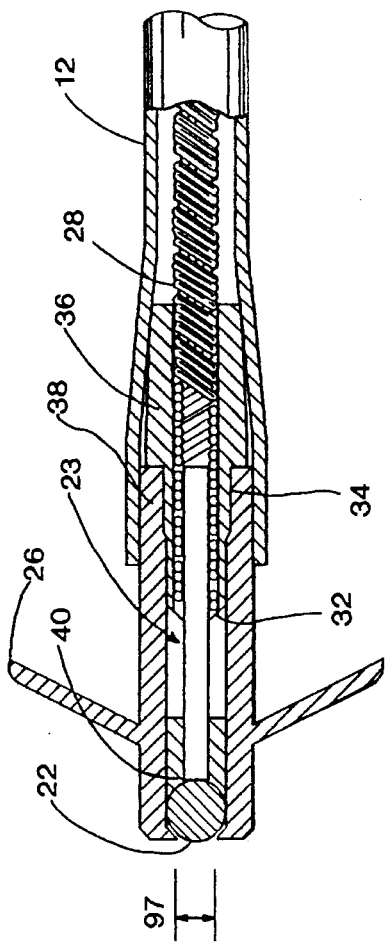
FIG. 1
FIG. 2
FIG. 3
(PRIOR ART)

MEDICAL ELECTRICAL LEAD HAVING A REINFORCED TINE ASSEMBLY

FIELD OF THE INVENTION

This invention relates to the field of body implantable medical electrical leads, and in particular to a body implantable medical electrical lead which features a reinforced tine assembly.

BACKGROUND OF THE INVENTION

In the medical field, various types of body implantable leads are known and used. One type of commonly used implantable lead is an endocardial pacing lead.

Endocardial pacing leads are attached at their proximal end to an implantable pulse generator and at their distal end to the endocardium of a cardiac chamber. The distal end of an endocardial lead may engage the endocardium by either an active fixation mechanism or a passive fixation mechanism.

Active fixation mechanisms use a structure, such as helix or hook, to physically engage into or actively affix themselves onto the heart. Passive fixation mechanisms, such as a tine assembly, lodge or passively fix themselves to the heart.

A preferred means for introducing an endocardial lead into the heart is through a vein. Specifically, such a lead, called a transvenous lead, is introduced into and maneuvered through the vein so the distal end is positioned within the heart. Generally, passive fixation leads are introduced into the heart in this manner, in particular, because the interior of the ventricular contains trabeculae which are easily and sufficiently engaged by tines.

One difficulty which has been encountered with such a design occurs from the packaging and handling of the tined leads before they are introduced into the patient. In particular, because it is necessary for the lead to be constructed from a pliant bio-compatible material, such as silicone, pre-implantation handling has been found on occasion to cause the lead structure to be deformed. In particular, it has been found that on occasion the tine assembly can be stretched or elongated so as to partially cover the electrode at the distal end of the lead. A partially covered electrode does not have the same electrical properties as if it were not covered. This may affect lead performance and ultimately affect the performance of the implantable pulse generator.

SUMMARY OF THE INVENTION

It is accordingly an object of the present invention to provide a medical electrical lead which has a reinforced tine assembly to prevent deformation due to lead handling.

This object is accomplished by providing a medical lead which has a reinforced tine assembly. In particular, the medical electrical lead of the present invention features an elongated lead body covered by an insulative sheath. Positioned upon the proximal end of the lead body is a terminal assembly. Terminal assembly permits the lead to be connected to a pulse generator. Positioned at the distal end of the lead body is an electrode. Also positioned proximate the electrode is a tine assembly. The tine assembly is preferably made from a insulative bio-compatible material, preferably silicone. The tine assembly further features a reinforcement to prevent the tine assembly from elongating. In the preferred embodiment, a polyester is used to provide reinforcement member.

DETAILED DESCRIPTION OF THE DRAWINGS

FIG. 1 shows a side plan view of an endocardial unipolar medical electrical lead according to the present invention;

FIG. 2 shows a cross-sectional view of the medical electrical lead shown in FIG. 1.

FIG. 3 shows a cross-sectional view of the medical electrical lead shown in FIG. 1 in which the tine assembly 38 has elongated and partially covers the electrode.

It should be noted the drawings are not necessarily to scale.

BRIEF DESCRIPTION OF THE DRAWINGS

As seen in FIG. 1, the medical electrical lead 1 of the present invention includes an elongated lead body 10 covered by an insulative sheath 12. Insulative sheath 12 may be fabricated of any flexible bio-compatible and bio-stable insulator. In the preferred embodiment silicone is used. Terminal assembly 14 is provided at the proximal end of lead 1. Terminal assembly 14 permits lead 1 to be coupled to a pulse generator (not shown.) Terminal assembly 14 is provided with sealing rings 16 in a terminal pin 18 all of a type know in the art. An anchoring sleeve 20 (shown partially in cross-section) slides over lead body 10 and serves as a point for suturing the lead body to body tissue at the insertion point of the lead into the vein or tissue in a fashion known in the art. Anchoring sleeve 20 and terminal assembly 14 may also be fabricated of any flexible bio-compatible and bio-stable material. In the preferred embodiment, anchoring sleeve 20 and terminal assembly 14 are fabricated from silicone.

Lead 1 shown in FIG. 1 further includes a stylet guide 11 and stylet assembly 13 coupled to the terminal pin 18. Styler assembly 13 imparts stiffness to the lead 1 during the insertion and placement of lead 1 transvenously into the heart. Stylet guide 11 and stylet assembly 13 are discarded after implantation of the lead into the heart and before connection of terminal pin 18 to a pulse generator (not shown).

At distal end of lead 10 a tine protector 15 is shown. Tine protector 15 is typically provided with the packaging of lead 1 to protect the tines until the lead is used. Specifically, tined protector 15 prevent tines 26 from being deformed during transit or storage of lead 1. Tines 26 are employed to passively retain electrode 22 in position within the heart as is well known in the pacing art.

As best seen in FIG. 2, lead 1 includes a multi-filar conductor coil 28 extending from terminal pin 18 to electrode 22. Electrode 22 is preferably a porous platinum ball covered with platinum black. In the preferred embodiment, the exposed surface of electrode 22 is generally hemispherical in shape. Although platinum is the preferred material for electrode 22 it may additionally include or be made entirely from various other materials, including but not limited to such materials as palladium, titanium, tantalum, rhodium, iridium, carbon, vitreous carbon and alloys, oxides and nitrides of such metals or other conductive materials. Electrode 22 is mounted at the end of metal pin 23. Metal pin 23 electrically engages conductor coil 28 through crimping at point 34 of crimping member 36. A silicone adhesive may be used at point 32 to seal the assembly against leakage of body fluids into the center lumen of insulative sheath 12 and coil 28. As seen, insulative sheath 12 covers crimping member 36 as well as tine assembly 38, which is fit between the distal end of insulative sheath 12 and the crimping member 34.

As seen in FIG. 2, a monolithic controlled release device (MCRD) 40 is positioned about metal pin 23 and next to electrode 22. MCRD is preferably loaded with an anti-inflammatory agent, e.g., asteroid dexamethasone sodium phosphate. The steroid is also deposited with the pores of the electrode 22 as is well known in the art, e.g. by application of a solution of 200 mg U.S.P. dexamethasone sodium phosphate dissolved in 5.0 cc isopropanol and 5.0 cc distilled or deionized water. Further details regarding the construction and loading of steroid into a MCRD and a electrode may be found in Stokes, U.S. Pat. No. 4,506,680 and related Medtronic U.S. Pat. Nos. 4,577,642; 4,606,118; 4,711,251 and 5,282,844, all incorporated herein by reference.

Electrode 22 is preferably constructed of a porous, sintered platinum having a porosity in the range of 0.5 to 100 microns. The porous platinum electrode material is further electroplated with platinum black. The platinum black electroplating is intended to reduce source impedance and polarization.

As seen, tine assembly 38 features tines 26 and reinforcement member 27. Tine assembly 38 is preferably constructed from silicone, although other biocompatible materials may be used, such as a polyether urethane, such as Pellethane ® CPR ® 2363-80AE available from the Upjohn Company. Reinforcement member 27 is provided so as to prevent the elongation of tine assembly 38 from a longitudinal force. As mentioned above, such a longitudinal force may be experienced when the lead 1 is removed from tine protector 15. As can be understood from reference to the Figures withdrawing the lead 1 from tine assembly 15 by movement proximally, depicted by arrow 99 in FIG. 1, tine assembly 38 may be caused to stretch or elongate such that the distal end of tine assembly 38 moves towards the very tip, or perhaps beyond, of electrode 22, as seen in FIG. 3. Through such an occurrence, the exposed macroscopic surface area of electrode 22 is reduced, thereby impacting upon the electrical characteristics of the lead. This can be best appreciated by comparing the exposed diameter 98 of electrode 22 shown in FIG. 2 (in which the lead features a reinforcement member 27 and the tine assembly 38 has not been stretched) with the exposed diameter 97 of electrode 22 shown in FIG. 3 (in which the lead does not feature a reinforcement member 27 and consequently tine assembly 38 has been stretched.) Because reinforcement number 27 imparts a longitudinal stiffness to tine assembly 38, it prevents the stretching or elongation of tine assembly 38 and thus partially covering of electrode 22.

In the preferred embodiment, reinforcement member 27 is polyester, although other materials such as nylon may also be used. The specific material used depends, in part, upon the composition of tine assembly 38. Reinforcement member 27 may either be constructed as a continuous cylinder or may be provided as a series of longitudinal members staggered about the diameter of tine assembly 38. Moreover while reinforcement member 27 has been depicted as positioned proximate inner lumen of tine assembly 38, reinforcement member 27 may further be positioned anywhere within or about tine assembly 38 to provide the requisite longitudinal reinforcement.

Although a specific embodiment of the invention has been disclosed, this is done for purposes of illustration only and is not intended to be limiting with regard to the scope of the invention. It is to be contemplated that various substitutions, alterations, and/or modifications may be made to the disclosed embodiment without departing from the spirit and scope of the invention as defined in the following claims. Such modifications or alterations may include providing the invention to a bipolar medical electrical lead and still further providing such longitudinal reinforcement to a diagnostic or therapeutic catheter.

What is claimed is:

1. A medical electrical lead comprising:

a connector assembly;

a coiled conductor having a distal end and a proximal end, the proximal end electrically coupled to the connector assembly;

an electrode electrically coupled to the distal end of the coiled conductor;

a insulative sheath covering the coiled conductor;

a tine assembly coupled to the insulative sheath at a first location spaced apart from the electrode, the tine assembly having a lumen, the tine assembly having at least one tine, the tine assembly having a cylindrical wall, the tine assembly having a longitudinal reinforcement member mounted within the cylindrical wall for preventing stretching or elongation of the tine assembly, the longitudinal reinforcement member is a cylinder member which encircles the lumen of the tine assembly, the longitudinal reinforcement member extending from a first point proximal relative to the first location, across the first location, to a second point distal relative to the first location.

2. A medical electrical lead according to claim 1 further comprising the reinforcement member is constructed of polyester.

3. A medical electrical lead according to claim 1 further comprising a monolithic controlled release device positioned proximate electrode.

4. A medical electrical lead according to claim 1 further comprising the electrode is constructed of a porous, sintered platinum having a porosity in the range of 0.5 to 100 microns.

5. A medical electrical lead according to claim 4 wherein the porous platinum electrode material is further electroplated with platinum black.

6. A medical electrical lead according to claim 1 further comprising drug dispensing means for dispensing a drug in the vicinity of the electrode, the drug dispensing means positioned within the lumen of the tine assembly.

7. A medical electrical lead according to claim 6 wherein the drug dispensing means dispenses a drug, the drug dispensed by the means for dispensing a drug is an anti-inflammatory agent.

8. A medical electrical lead according to claim 6 wherein the drug dispensing means dispenses a drug, the drug dispensed by the means for dispensing a drug is the sodium salt of dexamethasone phosphate.

9. A medical electrical lead according to claims 6 wherein the drug dispensing means dispenses a drug, the drug dispensing means comprises a water permeable polymer body located within the tine assembly and adjacent the electrode containing a water soluble form of the drug.

10. A medical electrical lead according to claim 1 wherein the electrode has an exposed surface, the exposed surface of the electrode is generally hemispherical in shape.

11. A medical electrical lead according to claim 1 wherein the electrode is formed of porous metallic or other conductive materials.

\* \* \* \* \*